United States Patent [19]

Verbrugge et al.

[11] 4,242,279

[45] Dec. 30, 1980

[54] 2-(2,2-DIHALOVINYL)-3,3-DIMETHYLCYCLOPROPYLACETONE PYRETHROID INTERMEDIATES

[75] Inventors: Pieter A. Verbrugge; Petrus A. Kramer, both of Amsterdam, Netherlands

[73] Assignee: Shell Oil Company, Houston, Tex.

[21] Appl. No.: 78,275

[22] Filed: Sep. 24, 1979

Related U.S. Application Data

[62] Division of Ser. No. 32,847, Apr. 24, 1979.

[30] Foreign Application Priority Data

Aug. 17, 1978 [GB] United Kingdom ............... 33763/78

[51] Int. Cl.$^3$ ............................................. C07C 49/23
[52] U.S. Cl. .................................... 568/303; 424/331; 560/231; 568/700; 568/420
[58] Field of Search ..................... 260/586 R; 424/331

[56] References Cited

U.S. PATENT DOCUMENTS

| | | | |
|---|---|---|---|
| 4,024,163 | 5/1977 | Elliott et al. ..................... | 260/465 D |
| 4,132,717 | 1/1979 | Roman ................................ | 260/546 |

FOREIGN PATENT DOCUMENTS 1413491  11/1975  United Kingdom .

Primary Examiner—Howard T. Mars
Assistant Examiner—Vera C. Clarke

[57] ABSTRACT

The invention relates to 2-(2,2-dihalovinyl)-3,3-dimethylcyclopropylacetones which are intermediates for the preparation of pyrethroids which have good insecticidal properties.

4 Claims, No Drawings

2-(2,2-DIHALOVINYL)-3,3-DIMETHYLCYCLO-PROPYLACETONE PYRETHROID INTERMEDIATES

This is a division of application Ser. No. 32,847, filed Apr. 24, 1979.

BACKGROUND OF THE INVENTION

1. Field of the Invention

The invention relates to a process for the preparation of an alkyl 2-(2,2-dihalovinyl)-3,3-dimethylcyclopropylacetate.

2. Description of the Prior Art

These compounds are useful as intermediate in the preparation of insecticidally active compounds starting from (+) 3-carene. These insecticidally active compounds are of the pyrethrin type and may, therefore, be called "pyrethroids". As these pyrethroids combine exceptionally good insecticidal properties with a very low mammalian toxicity, they are of great interest to the agrochemical industry and considerable effort has been directed at finding economic routes for their production. The esters of the 2-(2,2-dihalovinyl)-3,3-dimethylcyclopropanecarboxylic acids (hereinafter 2-(2,2-dichlorovinyl)-3,3-dimethylcyclopropanecarboxylic acid will also be referred to as "compound H") described in U.S. Pat. No. 4,024,163 are examples of pyrethroids. Compound H has the following structural formula:

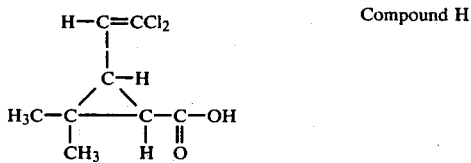

Compound H

3-Carene can, owing to the asymmetrical configurations at the 1- and 6-positions of the molecule, exist in the form of two optically active isomers, the (+) and the (−) configuration. The (+) configuration is an inexpensive, readily available, naturally occurring terpene found in numerous varieties of pine trees; it can be easily purified by fractional distillation.

The Applicants have found a simple process to prepare the above-mentioned intermediates in high yield.

SUMMARY OF THE INVENTION

Accordingly, the invention provides a process for the preparation of an alkyl 2-(2,2-dihalovinyl)-3,3-dimethylcyclopropylacetate, which process comprises two steps, the first step consisting in reaction of a tri(dialkylamino)phosphine or an alkyl ester of an ortho-phosphorous acid bis(dialkylamide) with a compound generating a dihalocarbene—which reaction is allowed to proceed to virtual completion—and the second step consisting in reaction of the product resulting from the first step with an alkyl 2-formyl-3,3-dimethylcyclopropylacetate, both steps being carried out in the presence of a solvent that is substantially inert or itself generates the dihalocarbene.

Surprisingly, the two-step process according to the invention affords the alkyl 2-(2,2-dihalovinyl)-3,3-dimethylcyclopropylacetates in a considerably higher yield than a one-step process comprising mixing the tri(dialkylamino)phosphine or alkyl ester of an ortho-phosporous acid bis(dialkylamide), the compound generating a dihalocarbene and the alkyl 2-formyl-3,3-dimethylcyclopropylacetate and allowing reaction of the mixture thus formed.

The alkyl groups present in the tri(dialkylamino)phosphine or the alkyl ester of an ortho-phosphorus acid bis(dialkylamide) may be the same or different and linear or branched. The alkyl groups are suitably the same and have preferably fewer than six, and more preferably fewer than three, carbon atoms. The use of tri(dialkylamino)phosphines is preferred, because these compounds usually afford the alkyl 2-(2,2-dihalovinyl)-3,3-dimethylcyclopropylacetates in a higher yield than the alkyl esters of ortho-phosphorous acid bis(dialkylamides) (the latter compounds are obtained by replacing one of the dialkylamino groups in a tri(dialkylamino)phosphine by an alkoxy group). Tri(diethylamino)phosphine and tri(dimethylamino)phosphine are most preferred.

Tri(dialkylamino)phosphines can easily be prepared by reaction of a dialkylamine with a phosphorus trihalide, as described in "Organic synthesis", Coll. Vol. V (1973) 602–603. This reaction results in the formation of a solution of the tri(dialkylamino)phosphine which also contains precipitated dialkylammonium halide. Filtration of the precipitate and distillation of the filtrate yields a fraction of pure tri(dialkylamino)phosphine. Applicant has tried to avoid the preparation of pure tri(dialkylamino)phosphine by contacting the solution containing the precipitate or the solution obtained after filtration of the precipitate, with the alkyl 2-formyl-3,3-dimethylcyclopropyl acetate, but this procedure afforded the alkyl 2-(2,2-dihalovinyl)-3,3-dimethylcyclopropylacetate in a very low yield only, if at all. It has now been found that this solution itself contains compounds which prevent the reaction with the alkyl 2-formyl-3,3-dimethylcyclopropyl acetate and that these compounds can easily be removed. Accordingly, a preferred embodiment of the present invention comprises reacting a dialkylamine with a phosphorus trihalide in the presence of a solvent that is substantially inert, washing the resulting reaction mixture with water (whether or not after prior separation of the precipitated dialkylammonium halide) and reacting the tri(dialkylamino)phosphine dissolved in the washed solution with the compound generating a dihalocarbene. This embodiment usually affords the alkyl 2-(2,2-dihalovinyl)-3,3-dimethylcyclopropylacetates in high yield. It is not necessary to separate the precipitated dialkylammonium halide prior to washing, because this salt is water-soluble. The yield of the alkyl 2-(2,2-dihalovinyl)-3,3-dimethylcyclopropylacetates can be further enhanced by drying the washed liquid, for example over a solid drying agent such as anhydrous sodium sulphate or anhydrous magnesium sulphate.

Another attractive feature of the process according to the present invention is that it may be carried out in the presence of alkane solvents, for example in alkane solvents with a boiling point or boiling range up to 200° C. This also applies to the said reaction between a dialkylamine and a phosphorus trihalide. Examples of alkane solvents are pentane, hexane, heptane, octane and nonane. Mixtures of alkanes are very suitable, for example gasolines having a boiling range from 62° C. to 82° C. or from 80° C. to 110° C. If desired, the process may be carried out in substantially inert solvents other than alkanes, for example in tetrahydrofuran.

The term "halo" used herein refers to fluoro, chloro, bromo and iodo. Examples of compounds generating a dihalocarbene under the conditions of the process according to the present invention are carbon tetrahalides, chloroform, bromoform and iodoform. Very good results have been obtained with carbon tetrahalides. Examples of carbon tetrahalides are carbon tetrachloride, carbon tetrabromide, carbon tetraiodide, bromotrichloromethane (forming dichlorocarbene) and dibromodifluoromethane (forming difluorocarbene). Very good results have been obtained with carbon tetrachloride.

Both steps of the process according to the present invention are preferably carried out at a temperature in the range of from about −50° C. to about +50° C., particularly at temperatures of from about −20° C. to about +35° C.

The alkyl group in the alkyl 2-formyl-3,3-dimethylcyclopropylacetates preferably has fewer than five carbon atoms; methyl 2-formyl-3,3-dimethylcyclopropylacetate—hereinafter also named "compound A'-'—is preferred. Compound A has the following structural formula:

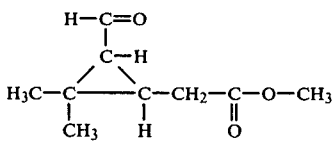

Compound A

The process may be carried out by adding a tri(dialkylamino)phosphine or an alkyl ester of an ortho-phosphorus acid bis(dialkylamide) to a compound generating a dihalocarbene, if desired dissolved in a solvent that is substantially inert, for example in an alkane solvent, and stirring the mixture thus obtained until the first step has been substantially completed, which may take from about 1 to about 60 minutes. Then, the alkyl 2-formyl-3,3-dimethylcyclopropylacetate is added to the mixture and stirring continued for about 1 to about 60 minutes until the second step has been completed. Dihalophosphoranes and phosphine oxides can be removed from the reaction mixture by washing. This washing can be carried out with water when tri(dimethylamino)phosphine has been used, but when a tri(dialkylamino)phosphine having two or more carbon atoms in the alkyl groups has been used, dilute aqueous hydrochloric acid is more suitable than water. Therefore, tri(dimethylamino)phosphine is the most preferred tri(dialkylamino)phosphine. The washed reaction mixture is dried and the solvent is evaporated from the dried solution to leave a residue, which may be further purified, for example by distillation, to obtain the alkyl 2-(2,2-dihalovinyl)-3,3-dimethylcyclopropylacetate in a pure state.

The preparation of the alkyl 2-formyl-3,3-dimethylcyclopropylacetates is described in British patent application Ser. No. 17269/78, filed May 2, 1978 and in applicants' concurrently filed U.S. patent application Ser. No. 32,848.

The alkyl 2-formyl-3,3-dimethylcyclopropylacetates and the alkyl 2-(2,2-dihalovinyl)-3,3-dimethylcyclopropylacetates have two asymmetric carbon atoms in the cyclopropane ring and may, therefore, have the 1R,cis, 1R,trans, 1S,cis or 1S,trans configuration. The nomenclature used herein to describe the spatial configurations has been defined by M. Elliott et al. in Nature, 248(1974) 710–711. It is an advantage of the process according to the invention that 1R,cis alkyl 2-formyl-3,3-dimethylcyclopropylacetates are fully converted into 1R,cis alkyl 2-(2,2-dihalovinyl)-3,3-dimethylcyclopropylacetates, because of the four spatial isomers of pyrethroid esters of the 2-(2,2-dihalovinyl)-3,3-dimethylcyclopropanecarboxylic acids it is the 1R,cis esters that usually have the highest pesticidal activity.

Alkyl 2-(2,2-dihalovinyl)-3,3-dimethylcyclopropylacetates are novel compounds. Among these novel compounds those in which the alkyl group has fewer than five carbon atoms are preferred. Among the four possible "halo" atoms, chloro and bromo and particularly chloro atoms are preferred. Methyl 2-(2,2-dichlorovinyl)-3,3-dimethylcyclopropylacetate—hereinafter also named "compound B"—is particularly preferred. Compound B has the following structural formula:

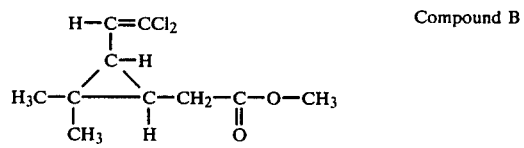

Compound B

Among the said four isomers of the alkyl 2-(2,2-dihalovinyl)-3,3-dimethylcyclopropylacetates the 1R,cis isomers is preferred.

2-(2,2-Dihalovinyl)-3,3-dimethylcyclopropanecarboxylic acids can be prepared as follows, starting from alkyl 2-(2,2-dihalovinyl)-3,3-dimethylcyclopropylacetates.

The alkyl 2-(2,2-dihalovinyl)-3,3-dimethylcyclopropylacetates can be hydrolyzed to the corresponding 2-(2,2-dihalovinyl)-3,3-dimethylcyclopropylacetic acids. For example, compound B can be hydrolyzed to 2-(2,2-dichlorovinyl)-3,3-dimethylcyclopropylacetic acid (herein also referred to as "compound C"). Compound C has the following structural formula:

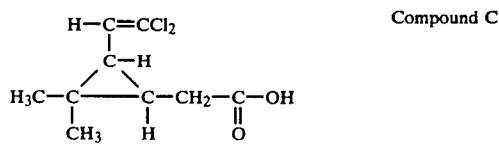

Compound C

Hydrolysis of esters is described in, for example, "Methoden der organischen Chemie" (Houben-Weyl), Volume VIII (1952), 418–423 and 638–639. Starting from the 1R,cis isomer of compound B this hydrolysis affords compound C exclusively in the 1R,cis configuration. The hydrolysis may, for example, be carried out with a solution of an alkali metal hydroxide in methanol or ethanol, followed by evaporation of the alcohol, addition of water to the residue obtained and acidification of the aqueous solution of the alkali metal salt of compound C.

The hydroxyl group in the 2-(2,2-dihalovinyl)-3,3-dimethylcyclopropylacetic acids can be converted into an alkyl group by reaction with an alkylmetal compound, followed by hydrolysis of the addition compound formed. The compounds thus obtained have the general formula:

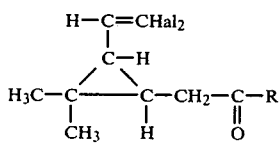  (I)

wherein R represents the alkyl group originating from the alkylmetal compound and Hal₂ represents two halogen atoms. Such reactions with alkylmetal compounds are described in "Methoden der organischen Chemie" (Houben-Weyl) Volume VII/2a (1973) 586–588. Suitable alkylmetal compounds are alkyllithium compounds; alkylmagnesium compounds may also be used. The alkyl group preferably has fewer than five carbon atoms and is particularly a methyl group. The reaction with the alkylmetal compound is suitably carried out in diethyl ether, an alkane solvent or tetrahydrofuran. Methylmetal compounds afford 2-(2,2-dihalovinyl)-3,3-dimethylcyclopropylacetones, for example 2-(2,2-dichlorovinyl)-3,3-dimethylcyclopropylacetone (hereinafter the latter compound is also named "compound D") Compound D has the following structural formula:

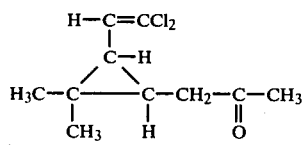 Compound D

Starting from the 1 R, cis isomers of the 2-(2,2-dihalovinyl)-3,3-dimethylcyclopropylacetic acids, the reaction with an alkylmetal compound, followed by hydrolysis of the addition compound formed, affords the compounds of formula I exclusively in the 1 R, cis configuration.

The compounds of the general formula I can be oxidized to compounds of the general formula:

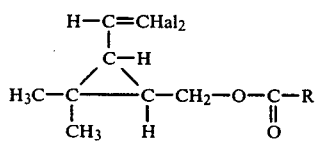  (II)

wherein R and Hal₂ have the same meaning as in the general formula I. Oxidation of ketones to esters is described in, for example, "Methoden der organischen Chemie" (Houben-Weyl), Volume VIII (1952) 559–560 and Volume VII/2b (1976) 1984–1986. The oxidation is suitably carried out with a peroxy acid, for example perbenzoic acid, 3-chloroperbenzoic acid, peracetic acid or perphthalic acid. Chloroform and acetic acid are suitable solvents. Oxidation of compound D yields 2-(2,2-dichlorovinyl)-3,3-dimethylcyclopropylmethyl acetate (hereinafter also named "compound E") Compound E has the following structural formula:

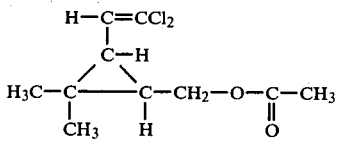 Compound E

Starting from the 1 R, cis isomers of the compounds of formula I, the compounds of formula II are obtained essentially exclusively in the 1 R, cis configuration.

Compounds of the general formula II can be hydrolyzed to 2-(2,2-dihalovinyl)-3,3-dimethylcyclopropylmethanol, for example to 2-(2,2-dichlorovinyl)-3,3-dimethylcyclopropylmethanol (hereinafter the latter compound is also referred to as "compound F"). Starting from the 1 R, cis isomer of a compound of the general formula II this hydrolysis affords the 2-(2,2-dichlorovinyl)-3,3-dimethylcyclopropylmethanols exclusively in the 1 R, cis configuration. The structural formula of compound F is as follows:

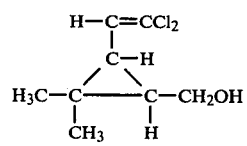 Compound F

The 2-(2,2-dihalovinyl)-3,3-dimethylcyclopropylmethanols may be oxidized via 2-(2,2-dihalovinyl)-3,3--dimethylcyclopropanecarbaldehydes—for example to 2-(2,2-dichlorovinyl)-3,3-dimethylcyclopropanecarbaldehyde, which is hereinafter also named "compound G"—to 2-(2,2-dihalovinyl)-3,3-dimethylcyclopropanecarboxylic acids, for example to compound H, with an agent oxidizing a hydroxymethyl group to a carboxyl group. Compound G has the following structural formula:

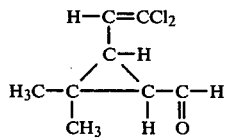 Compound G

This oxidation may be carried out with a peroxy acid, for example perbenzoic acid or 3-chloroperbenzoic acid. Further methods for such oxidations are described in, for example, "Methoden der organischen Chemie" (Houben-Weyl) Volume VIII(1952) 407–413.

The following compounds are novel compounds:
the 2-(2,2-dihalovinyl)-3,3-dimethylcyclopropylacetic acids and their salts, for example their alkali metal salts,
the compounds of the general formula I,
the compounds of the general formula II,
the 2-(2,2-dihalovinyl)-3,3-dimethylcyclopropylmethanols and
the 2-(2,2-dihalovinyl)-3,3-dimethylcyclopropanecarbaldehydes.

In the novel compounds of this application "halo" or "halogen" means halogen of atomic number 9 through 35, inclusive, for example, chlorine, fluorine or bromine.

Among these novel compounds compound C, the salts of compound C (for example the alkali metal salts), compound D, compound E, compound F and compound G are preferred. Among the four possible configurations of all of these compounds the 1 R, cis isomers are preferred, because, as stated, among these four spatial isomers of pyrethroid esters of the 2-(2,2-dihalovinyl)-3,3-dimethylcyclopropanecarboxylic acids it is the 1 R, cis esters that have the highest pesticidal activity.

The following Examples further illustrate the invention. The nuclear magnetic resonance (NMR) data quoted were recorded at 90 MHz using solutions of the compounds in deuterochloroform with tetramethylsilane as the internal standard.

EXAMPLE I

Preparation of 1 R, cis compound B

Tri(dimethylamino)phosphine (6.2 mmol) was added at once with stirring at a temperature of $-10°$ C. to a solution of carbon tetrachloride (5.8 mmol) in pentane (15 ml), present in a three-necked round-bottomed flask provided with a dropping funnel, magnetic stirrer, thermometer, reflux condenser, calcium chloride tube and an inlet for nitrogen. The temperature was allowed to rise to $+10°$ C., which resulted in the formation of a white precipitate. All of this precipitate was formed at once. This indicated the end of the first step. The suspension was cooled to $-10°$ C., at which temperature 1 R, cis compound A (2.9 mmol) was added. Then the temperature was allowed to increase to $+10°$ C. over a period of 10 min. This ended the second step. The reaction mixture was washed with water (75 ml), the washed liquid was dried over anhydrous sodium sulphate and the solvent was evaporated from the dried liquid, leaving a residue (0.55 g) which contained compound B (100% 1 R, cis) in a yield of 81%.

The NMR spectrum of compound B showed the following absorptions:

| | | | |
|---|---|---|---|
| $\delta$ = 1.03 ppm singlet | H$_3$C—C—CH$_3$ | $\delta$ = 1.19 ppm singlet | H$_3$C—C—CH$_3$ |
| $\delta$ = 1.55 ppm double doublet | HC—CH=C | $\delta$ = 1.35 ppm multiplet | HC—CH$_2$ |
| $\delta$ = 2.33 ppm doublet | J = 7.5Hz HC—CH$_2$ | $\delta$ = 3.71 ppm singlet | OCH$_3$ |
| $\delta$ = 5.53 ppm doublet | J = 8Hz CH=C | | |

The optical rotation of a solution of compound B in methanol was $[\alpha]_D^{20} = +32.2°$, concentration 15.39 g/l in methanol.

EXAMPLE II

Preparation of 1 R, cis compound C

A mixture obtained by adding potassium hydroxide (45 mmol) to a solution of 1 R, cis compound B (4.2 mmol) in methanol (20 ml) was heated with stirring under reflux for 45 min. Then, the mixture was allowed to adopt ambient temperature (20° C.), the methanol was evaporated, water (100 ml) was added to the residue obtained and the mixture formed was extracted with three 20-ml portions of dichloromethane. The aqueous raffinate phase was acidified with concentrated hydrochloric acid and the acidified solution was extracted with three 20-ml portions of dichloromethane. The combined extract phases were dried over anhydrous magnesium sulphate and the solvent was evaporated from the dried liquid, leaving a residue (0.75 g) which contained compound C (100%, 1 R, cis) in a yield of 80%.

The NMR spectrum of compound C showed the following absorptions:

| | | | |
|---|---|---|---|
| $\delta$ = 1.08 ppm singlet | H$_3$C—C—CH$_3$ | $\delta$ = 1.22 ppm singlet | H$_3$C—C—CH$_3$ |
| $\delta$ = 1.30 ppm multiplet | HC—CH$_2$ | $\delta$ = 1.60 ppm double doublet | HC—CH=C |
| $\delta$ = 2.38 ppm doublet | HC—CH$_2$, J = 7.5Hz | $\delta$ = 5.58 ppm doublet | CH=C, J = 9Hz |
| $\delta$ = 11.35 ppm broad singlet | —COOH | | |

EXAMPLE III

Preparation of 1 R, cis compound D

A 2 M solution (0.5 ml) of methyllithium in diethyl ether was added with stirring at 20° C. to a solution of 1 R, cis compound C (0,11 mmol) in diethyl ether (2.5 ml). After stirring for 105 min diethyl ether (20 ml) was added, the mixture was washed neutral with 0,1 N hydrochloric acid and after separating off the water layer, the organic phase was dried over anhydrous magnesium sulphate. Evaporation of the solvent from the dried liquid left a residue (26 mg) which contained compound D (100% 1 R, cis) and 1-[2-(2,2-dichlorovinyl)-3,3-dimethylcyclopropyl]-2-methylpropan-2-ol (100% 1 R, cis, both in a yield of 50%.

The NMR spectrum of compound D showed the following absorptions:

| | | | |
|---|---|---|---|
| $\delta$ = 0.99 ppm singlet | H$_3$C—C—CH$_3$ | $\delta$ = 1.18 ppm singlet | H$_3$C—C—CH$_3$ |
| $\delta$ = 1.50 ppm multiplet | HC—CH$_2$ and HC—CH=C | $\delta$ = 2.20 ppm singlet | C(O)—CH$_3$ |
| $\delta$ = 2.41 ppm doublet | HC—CH$_2$, J = 7Hz | $\delta$ = 5.53 ppm doublet | CH=C, J = 9Hz |

The NMR spectrum of 1-[2-(2,2-dichlorovinyl)-3,3-dimethylcyclopropyl]-2-methylpropan-2-ol showed the following absorptions:

| | | | |
|---|---|---|---|
| $\delta$ = 1.02 ppm singlet | H$_3$C—C—CH$_3$ | $\delta$ = 1.19 ppm singlet | H$_3$C—CH—CH$_3$ |
| $\delta$ = 1.27 ppm singlet | H$_3$C—C(OH)—CH$_3$ | $\delta$ = 1.51 ppm doublet | HC—CH$_2$, J = 7Hz |
| $\delta$ = 1.5 ppm multiplet | HC—CH$_2$ and HC—CH=C | $\delta$ = 5.60 ppm doublet | CH=C, J = 9Hz |

-continued

| | |
|---|---|
| δ = 1.90 ppm broad singlet | —CO<u>H</u> |

EXAMPLE IV

Preparation of 1 R, cis compound E

3-Chloroperbenzoic acid (0,098 mmol) was added to a solution of the residue obtained in Example III (26 mg, containing 0,05 mmol of compound D) in deuterochloroform (0.3 ml). After 16 hours' stirring at 20° C. the conversion of compound D was 25%. Then, 3-chloroperbenzoic acid (0,25 mmol) was again added, the mixture was warmed up to 40° C. and stirring was continued. The conversion of compound D was 85% after 7 hours' and 100% after 60 hours' stirring. The mixture obtained was washed with a saturated aqueous solution of sodium hydrogen carbonate. The washed solution contained compound E (100% 1 R, cis, yield 100%, calculated on starting compound D) and 1-[2-(2,2-dichlorovinyl)-3,3-dimethylcyclopropyl]-2-methylpropan-2-ol.

The NMR spectrum of compound E showed the following absorptions:

| | |
|---|---|
| δ = 1.09 ppm singlet | H₃C—C—C<u>H</u>₃ |
| δ = 1.60 ppm multiplet | <u>H</u>C—CH₂ and <u>H</u>C—CH═C |
| δ = 4.12 ppm doublet | <u>H</u>₂C—O—, J = 7Hz |

EXAMPLE V

Preparation of 1 R, cis compound F

The solvent was evaporated from the washed solution containing compound E obtained in Example IV, the residue formed was mixed with potassium hydroxide (2 mmol) and methanol (1 ml) and the mixture obtained was boiled for one hour. Then, the mixture was diluted with water (5 ml), the diluted mixture was extracted with three 2-ml portions of dichloromethane and the combined extract phases were dried over anhydrous magnesium sulphate. Evaporation of the solvent from the dried liquid left a residue (16 mg) which contained compound F (100%, 1 R, cis) in a yield of 90%. 1-[2-(2,2-Dichlorovinyl)-3,3-dimethylcyclopropyl]-2-methylpropan-2-ol was also present in the residue.

The NMR spectrum of compound F showed the following absorptions:

| | |
|---|---|
| δ = 1.12 ppm singlet | H₃C—C—C<u>H</u>₃ |
| δ = 1.28 ppm multiplet | <u>H</u>C—CH₂ |
| δ = 3.67 ppm doublet | —CH₂O<u>H</u>, J = 7.5Hz |
| δ = 1.90 ppm broad singlet | —O<u>H</u> |

| | |
|---|---|
| δ = 1.20 ppm singlet | H₃C—C—C<u>H</u>₃ |
| δ = 1.59 ppm double doublet | <u>H</u>C—CH═C |
| δ = 5.65 ppm doublet | C<u>H</u>═C, J = 9Hz |

EXAMPLE VI

Preparation of 1 R, cis compound H

The residue obtained in Example V (containing 0.04 mmol of 1 R, cis compound F and 0.03 mmol of 1 R, cis 1-[2-(2,2-dichlorovinyl)-3,3-dimethylcyclopropyl]-2-methylpropan-2-ol) was mixed with deuterochloroform (0.3 ml), 2,2,6,6-tetramethylpiperidine (2-microliters) and 3-chloroperbenzoic acid (0.12 mmol). After 1.5 hours' stirring at 20° C. compound F had been completely converted into compound G.

The NMR spectrum of compound G showed the following absorptions:

| | |
|---|---|
| δ = 1.30 ppm singlet | H₃C—C—C<u>H</u>₃ |
| δ = 2.25 ppm multiplet | <u>H</u>C—C(O) |
| δ = 9.66 ppm doublet | —C(O)<u>H</u>, J = 3Hz |

| | |
|---|---|
| δ = 1.55 ppm multiplet | <u>H</u>C—CH═C |
| δ = 6.22 ppm doublet | C<u>H</u>═C, J = 8Hz |

Then, 3-chloroperbenzoic acid (0.12 mmol) was added to the mixture. After 2 hours' stirring at 20° C. compound G had been converted into compound H (100%, 1 R, cis yield 30%).

What we claim is:

1. A compound of the formula:

$$\begin{array}{c} H-C\!\!=\!\!CHal_2 \\ | \\ C\!-\!H \\ / \quad \backslash \\ H_3C\!-\!C\!\!-\!\!\!-\!\!\!-\!\!\!-\!\!C\!-\!CH_2\!-\!C\!-\!R \\ | \quad\quad\quad | \quad\quad \| \\ CH_3 \quad\quad H \quad\quad O \end{array}$$

wherein R represents an alkyl group containing from 1 to 4 carbon atoms and Hal₂ two halogen atoms having an atomic number of from 9 to 35.

2. A compound according to claim 1 wherein each Hal is chlorine.

3. A compound according to claim 2 in which R represents a methyl group.

4. A compound according to claims 1, 2 or 3 which is in the 1R,cis form.

* * * * *